United States Patent
Tayot et al.

(12) 
(10) Patent No.: US 6,391,939 B2
(45) Date of Patent: *May 21, 2002

(54) COLLAGENIC MATERIAL USEFUL IN PARTICULAR FOR PREVENTING POST-OPERATIVE ADHESIONS

(75) Inventors: Jean-Louis Tayot, La Tour de Salvagny; Michel Tardy, Lyons; Philippe Gravagna, Irigny, all of (FR)

(73) Assignee: Imedex Biomateriaux, Chaponost (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,842
(22) PCT Filed: Feb. 5, 1998
(86) PCT No.: PCT/FR98/00214
§ 371 Date: Aug. 5, 1999
§ 102(e) Date: Aug. 5, 1999
(87) PCT Pub. No.: WO98/34656
PCT Pub. Date: Aug. 13, 1998

(30) Foreign Application Priority Data

Feb. 6, 1997 (FR) .............................................. 97 01373
Sep. 17, 1997 (FR) .............................................. 97 11589

(51) Int. Cl.$^7$ ............................................... A61L 31/00
(52) U.S. Cl. ..................... 523/105; 523/106; 523/111; 524/17; 524/18; 524/21; 524/27; 524/28; 524/35; 524/47; 524/54; 524/56; 524/58; 527/101; 527/200; 522/87; 522/88
(58) Field of Search ................. 527/200, 101; 522/87, 88; 523/105, 106, 111; 524/17, 18, 21, 27, 28, 35, 47, 54, 56, 58

(56) References Cited

U.S. PATENT DOCUMENTS 4,931,546 A * 6/1990 Tardy et al.
5,114,627 A * 5/1992 Civerchia
5,201,745 A 4/1993 Tayot et al.
5,580,923 A 12/1996 Yeung et al.
5,618,551 A 4/1997 Tardy et al.
5,931,165 A 8/1999 Reich et al.

FOREIGN PATENT DOCUMENTS

| EP | 0 732 110 | 9/1996 |
| FR | 2 715 309 | 7/1995 |
| FR | 2 720 945 | 12/1995 |
| WO | 96/08277 | 3/1996 |

OTHER PUBLICATIONS

Wiseman et al., Fibrinolytic Drugs Prevent Pericardial Adhesions in the Rabbit, Journal of Surgical Research, vol. 53, pp. 362–368 (1992).
Wiseman, David, Polymers for the Prevention of Surgical Adhesions, Polymeric Site–specific Pharmacotherapy, pp. 370–421 (1994).
Becker et al., Prevention of Postoperative Abdominal Adhesions By A Sodium Hyaluronate–Based Bioresorbable Membrane: A Prospective, Radomized, Double–Blind Multicenter Study, Journal of the American College of Surgeons, vol. 183, pp. 287–306 (Oct., 1996).
Harris et al., Analysis of the Kinetics of Peritoneal Adhesion Formation in the Rat and Evaluation of Potential Antiadhesive Agents, Surgery, vol. 117, No. 6, pp. 663–669 (Jun., 1995).
diZerega M.D., Gere S., Contemporary Adhesion Prevention, Fertility and Sterility, vol. 61, No. 2, pp. 219–235 (Feb., 1994).

* cited by examiner

*Primary Examiner*—Susan W. Berman
(74) *Attorney, Agent, or Firm*—Larson & Taylor PLC

(57) ABSTRACT

The present invention relates to a biocompatible collagenous material which is non-toxic and biodegradable in less than one month, preferably in less than one week. This material comprises collagen and at least one hydrophilic macromolecular additive which is chemically non-reactive towards the collagen, with the collagen having at least partially lost its helical structure and being crosslinked. The invention also relates to a process for obtaining such a material. The collagenous material according to the invention is used, in particular, for preventing post-operative adhesions.

107 Claims, No Drawings

COLLAGENIC MATERIAL USEFUL IN PARTICULAR FOR PREVENTING POST-OPERATIVE ADHESIONS

The present invention relates to a biocompatible, non-toxic collagenous material which is potentially adherent and rapidly biodegradable. It relates more specifically to a collagenous material which is able to inhibit the formation of post-operative adhesions.

The invention also relates to a process for obtaining such a material.

Post-operative adhesions develop following surgical intervention in a patient, certain of whose organs have been subjected to trauma engendered by the surgical act itself.

The wounds created by dissecting organs or tissues, or by any other intervention, are characterized by two phenomena:

these wounds are not watertight and spontaneously exude a plasma fluid containing fibrin, sometimes even blood, if perfect haemostasis has not been achieved; certain organs ooze other liquids such as liver bile or cerebrospinal fluid in the case of the nervous system.

the damaged surfaces no longer possess an organized and stable tissue barrier and are occasionally even strewn with foreign bodies: suture threads, staples, blood clots, infectious agents, or tissues burnt by diathermy knives or laser beams.

These two characteristics bring about a reaction in the organism which starts with inflammation and continues with an intense and generally poorly organized migration and proliferation of cells. These usually give rise to neo-formed, fibrous, vascularized tissues which connect the damaged organs to adjacent organs.

Many reviews have been published on the subject (see, in particular, DI ZEREGA (1994)).

A variety of solutions have already been proposed, particularly at the pharmacological level, with varying degrees of success.

The most effective solution known to date is to place on the wound a physical barrier which isolates the organs from each other and which allows them to cicatrize independently without developing inter relationships.

Artificial, non-degradable tissues, to which cells do not attach, constitute the physical barriers which lead to the best results. Teflon® and silicone are examples of the most efficient polymers.

The major drawback is that these physical barriers have to be removed, several weeks later, by means of a second surgical operation which can, furthermore, itself give rise to other secondary adhesions at the site of the laparotomy.

It is therefore vital to develop biodegradable barriers which avoid the necessity of a second intervention.

With this aim in mind, a large number of natural biodegradable polymers made from gelatin, collagen, polysaccharides, mucopolysaccharides, etc. have already been proposed; however, these polymers have not led to satisfactory results.

According to RODEHEAVER's team (HARRIS et al., 1995), the minimum objective is that the barrier should remain in place for at least 36 hours. This is explained by the fact that a minimum time is required to enable the complex mechanisms of cicatrization to take their course.

However, the resorption time should not be too long. If the material remains in contact with the wound for several weeks it can give rise to persistent inflammatory reactions which favour a disorganized and more substantial fibrous reaction and which can cause anatomical problems locally: thickness, rigidity, shrinkage, ischaemia, granuloma or a persistent focus of infection, particularly in contact with the intestines and the digestive organs.

Furthermore, it appears that the material which is to serve as a physical barrier should adhere correctly to the damaged tissues, in particular when protecting organs which are mobile or which are subjected to variable distension, such as the intestine, or simply to prevent the barrier migrating in response to the movements of the patient and to the mechanical constraints which these movements entail.

The difficulty of obtaining all these properties combined in one and the same biomaterial explains why the solutions and products proposed to date are still found to be very inadequate.

The biodegradable products which are currently marketed for preventing adhesions are only partially active and yield results which are still inadequate.

The cellulose derivatives which are marketed by Johnson & Johnson Medical (Arlington, Tex., United States), such as the products SURGICELL® or INTERCEED®, cannot be used in the presence of blood and give disappointing results in some animal models (HARRIS et al., 1995).

The product SEPRAFILM®, which is marketed by Genzyme, (Cambridge, Mass., United States), is a film composed of hyaluronic acid and carboxymethyl cellulose and which only appears to be effective in 50% of cases (BECKER et al., 1996). While it degrades very rapidly in a few days, it is difficult to manipulate. It is fragile and brittle and impossible to use through a trocar in association with laparoscopy. Finally, it progressively loses its initial adherence and can migrate some distance, thereby leaving the wound unprotected.

The products which have been recently described by research workers in the literature or in published patent applications still appear to leave a large number of problems unresolved.

Products which have been recently proposed include a variety of collagenous materials.

KHOURY et al. (1994) propose, on behalf of COLETICA (Lyon, France), a collagen membrane which consists of two layers, with one layer being based on native collagen and forming the support and being covered with a second layer of gelatin. The idea for this membrane is inspired by a visceral surgery patch which was developed by TAYOT et al. (1988). This material has a degradation time which is very much longer than one month and does not, therefore, possess the essential property, which is that of disappearing very rapidly. It also suffers from the drawback of not being sufficiently adherent and, as a consequence, of having to be applied with suture stitches, which can give rise to undesirable complications.

In 1994, ORLY I. (6) proposed, on behalf of COLETICA, a transparent collagen membrane which consists of a single layer or of two layers, depending on the examples, and is usually combined with an undegradable prosthesis for treating hernias or eventrations. This membrane consists of undenatured native collagen. It has to be stapled or sutured. In order to make the stapling easier, it is necessary for the membrane to be transparent in order to avoid injuring sensitive zones (nerves and blood vessels), as in the case of inguinal hernias. The risks associated with stapling hernial prostheses, in particular, are well known. For this reason, surgeons will be more interested in gluing these prostheses, thereby avoiding any sutures or staples. ORLY I. specifies, surprisingly, that this membrane should not be adhesive since it is not possible to use the membrane developed by KHOURY et al., in the same Company, i.e. COLETICA (cited above), in this indication due to its adhesive properties, which hinder insertion in association with abdominal surgery. The time taken for resorption in the case of this membrane is considerably longer than one month since resorption is not complete at 5 weeks and 3 months are required for the material to have been almost totally eliminated. Despite these very long periods, the Applicant asserts, paradoxically, that the material has the advantage of a "relatively" rapid resorption time.

In 1995, YEUNG et al. (7) proposed, on behalf of Collagen Corporation (Palo Alto, Calif., United States), linking an anti-adhesion agent derived from polyethylene glycol to a collagenous substrate by means of covalent bonds. This product is very complicated to produce and requires the use of polyethylene glycol derivatives which are difficult to manufacture, expensive and not devoid of toxic risks associated with their chemical reactivity. Finally, the resorption time which is indicated for this material consisting of dense collagen is usually from 30 to 50 days.

In 1994, TARDY et al. (8) proposed, in a patent on behalf of IMEDEX, now called SADUC, a liquid biological glue which is derived from collagen and which has anti-adhesion properties. The particular advantages of this product are its adherence and its rapid degradation within a few days. The adhesive properties stem from the crosslinking of the molecules of collagen, which is oxidized with periodic acid and which is stored liquid at acid pH. This crosslinking is triggered by adding an alkaline solution, or a buffer, which neutralizes the pH and which rapidly transforms the solution of oxidized collagen into an adherent solid. Nevertheless, the efficacy of this product in preventing post-operative adhesions, which has been demonstrated in several animal models, is not easy to exploit in practice. Thus, this product has to be stored permanently in frozen form, something which is difficult to achieve in current hospital systems.

Various collagenous biomaterials obtained by crosslinking collagen following oxidation with periodic acid were also described by M. TARDY et al. (9) in a patent in 1986. Films of crosslinked oxidized collagen were prepared by drying solutions of oxidized collagen, to which glycerol had been added, under a stream of sterile air. These films have properties which depend on the quantity of glycerol employed. In order to obtain pliable, non-brittle films which possess acceptable resistance, a sufficient quantity of glycerol, approximately equal in weight to the quantity of collagen, has to be used. However, under these conditions, the films stick to their support and to the surgeon's gloves and instruments, lack rigidity because of their delicacy and are very difficult to use if they are not combined with another material.

The invention described below makes it possible to resolve the previously mentioned drawbacks.

The particular object of the invention is to provide a biocompatible material which is non-toxic and non-sticky to the touch in the dry state for ease of manipulation, but which is able to develop adhesive properties in an aqueous medium, in particular in a physiological medium.

Another object of the invention is to provide a material which is rapidly biodegradable, namely in less than one month and, preferably, in less than one week.

Another object of the invention is to provide a collagenous material which is suitable for use as a post-operative anti-adhesion barrier.

Another object of the invention is to provide a process for obtaining such a material.

To this end, the invention relates to a biocompatible collagenous material which is non-toxic and biodegradable in less than one month, characterized in that it comprises collagen, which has at least partially lost its helical structure, and at least one hydrophilic macromolecular additive which is chemically non-reactive towards the collagen, with the collagen being crosslinked.

The invention also relates to such a material which is biodegradable within less than one week.

The invention also relates to a process for obtaining a biocompatible collagenous material which is non-toxic, potentially adherent and biodegradable in less than one month, preferably in less than one week, characterized in that it comprises:

a) preparing a collagen solution;
b) treating the said solution in order to cause the collagen at least partially to lose its helical structure;
c) mixing the resulting collagenous solution with a solution containing at least one hydrophilic macromolecular additive which is chemically non-reactive towards the collagen which is present;
d) crosslinking the said mixture in order to obtain the desired collagenous material.

The inventors discovered, surprisingly, that a mixture of collagen, which had been denatured by moderate heating, and a hydrophilic macromolecular additive was able, after the collagen had been crosslinked, to form a biocompatible and non-toxic material which was, at one and the same time, non-sticky to the touch in the dry state, adherent in an aqueous (physiological) medium, and biodegradable in a few days or a few weeks.

They demonstrated that it was possible to obtain such a material by crosslinking the collagen, which had been previously modified by oxidative cleavage and heating, in the presence of a hydrophilic macromolecular additive which was chemically non-reactive towards the collagen.

While the function of the oxidative cleavage of the collagen is to permit subsequent moderate crosslinking of the collagenous material, the invention does not exclude the possibility of achieving this function of moderate crosslinking by other means, for example by beta or gamma radiation, or using other agents for achieving moderate crosslinking, for example using chemical agents in amounts which are sufficiently low and non-toxic.

While the treatment consisting of heating the collagen solution at a temperature greater than 37° C. leads to the progressive loss of the helical structure of the collagen, the invention does not exclude the possibility that this function can be achieved by other physical or chemical means, for example by means of ultrasonication, or by means of adding chaotropic agents.

The inventors discovered, in particular, that the presence of the hydrophilic additive unexpectedly made it possible to increase the density and mechanical resistance of the collagen and to render the collagen potentially adhesive, that is to say to permit satisfactory adhesiveness, in particular in a physiological medium, to organs and to promote degradation of the collagen, which degradation can thus be accomplished, according to the embodiments of the invention, in less than seven days or less than 4 weeks.

The process for preparing a collagenous material according to the present invention is described below.

The collagen which is used for obtaining a collagenous material as previously defined can equally well be of animal or human origin or obtained by means of genetic recombination. Use is preferably made of native collagen which has been solubilized at acid pH or after digestive treatment with pepsin. The collagen can, in particular, be bovine type I collagen or human type I or type III collagen or else mixtures of the latter collagens in any proportions.

According to one embodiment of the invention, the collagen is modified by means of oxidative cleavage. Periodic acid or one of its salts can be used for this purpose, in accordance with the technique described by M. TARDY et al. (1986).

It may be recalled, briefly, that this technique consists in subjecting an acid solution of collagen to the action of periodic acid or one of its salts by mixing the collagen solution with a solution of this acid or salt at a concentration of between 1 and $10^{-5}$ M, preferably between $5 \times 10^{-3}$ M and $10^{-1}$ M, at a temperature in the vicinity of ambient temperature and for a period which can range from 10 minutes to 72 hours.

According to the invention, an acid solution of collagen is used whose concentration is between 5 and 50 g/l. The concentration of collagen is preferably 30 g/l.

This treatment induces cleavages in certain constituents of the collagen, i.e. hydroxyproline and sugars, and thus creates reactive sites without thereby inducing crosslinking.

The oxidized collagen, which has thus been prepared in solution, is heated at a temperature greater than 37° C., preferably at a temperature of between 40 and 50° C. This results in the helical structure of the collagen being at least partially denatured.

The collagen is then crosslinked in the presence of at least one hydrophilic macromolecular additive which is chemically non-reactive towards the collagen.

"Chemically non-reactive towards the collagen" is understood as meaning a hydrophilic compound which is not able to react with the collagen which is present and which in particular does not form any covalent bond with the collagen while it is being crosslinked.

The hydrophilic macromolecular additive according to the invention advantageously has a molecular weight which is greater than 3000 daltons.

The hydrophilic additive can be a synthetic hydrophilic polymer advantageously having a molecular weight of between 3000 and 20,000 daltons. Polyethylene glycol is particularly preferred.

The hydrophilic additive can also be a polysaccharide, among which may be mentioned starch, dextran and cellulose, which are preferred.

It is also possible to envisage using those polysaccharides, which, in oxidized form, display carboxylic functions in these molecules.

While mucopolysaccharides may also be suitable for the aims of the invention, they are not preferred because their distinctive animal origin renders them difficult to prepare while satisfying the prescribed standards of traceability.

The hydrophilic additive is selected according to a variety of parameters which are linked, in particular, to its use, such as its price, its harmlessness, its biodegradability and/or its ability to be eliminated, in particular via the kidneys, in the event of therapeutic use.

The said crosslinking is achieved by mixing, at neutral pH, a solution of collagen, which has been modified by oxidative cleavage and heating as indicated above, with a solution containing at least one hydrophilic macromolecular additive.

The concentration of hydrophilic additive(s) is from 2 to 10 times lower than that of the collagen.

The crosslinking of the collagen in the presence of the hydrophilic additive is effected at a temperature of between 4 and 30° C., preferably at from 18 to 25° C.

According to one embodiment, the crosslinking is envisaged to be carried out in the presence of glycerol, which can be added to the collagen/hydrophilic additive mixture. In this case, the concentration of glycerol is advantageously between 3 and 8 g/l, and does not exceed one third of the concentration of the collagen.

The polymerization takes place while the material is drying.

According to the invention, it is thought, without it being possible for this to be regarded as being limiting, that the hydrophilic additive which is present during the crosslinking of the collagen is contained in the collagenous network which is formed, even though it does not itself react with the collagen.

According to the envisaged applications, the crosslinked collagenous material can be subjected to a variety of standard treatments such as drying, sterilization, etc.

The crosslinked collagen can be dried, in particular, in a stream of sterile air, if this is required.

Sterilization is advantageously implemented by means of irradiation with beta radiation (irradiation with electrons) or gamma radiation (irradiation using radioactive cobalt).

In accordance with the invention, the collagenous material can be prepared in the form of a film, a gel or a paste.

According to the applications which are envisaged, the collagenous material is advantageously conceived in the form of a film.

According to one particularly preferred embodiment, the solution containing the collagen, which has at least partially lost its helical structure, in particular as a result of heating, and, where appropriate, has been modified by oxidative cleavage, a hydrophilic macromolecular additive and, where appropriate, glycerol, is distributed uniformly on an inert support, which is substantially flat, in order to form a crosslinked film.

The support is inert in that it does not react with the abovementioned compounds and is not involved in the crosslinking process. A hydrophobic support of the PVC or polystyrene type can be used.

In this case, a solution in which the concentrations of collagen, of hydrophilic additive and of glycerol, if it is present, are preferably between 2 and 6% in the case of collagen, 0.6 and 2% in the case of the hydrophilic additive, and 0.3 and 0.8% in the case of the glycerol, is applied to the support.

The thin layer which is applied advantageously has a density of from 0.05 to 0.3 $g/cm^2$.

Once the reaction is complete, the film is separated from the support.

The collagenous material according to the invention contains collagen and at least one hydrophilic macromolecular additive in accordance with a collagen/hydrophilic additive(s) ratio of from 1/1 to 9/1, preferably of from 2/1 to 4/1 and, still more preferably, of 3/1.

The collagenous material is stable at ambient temperature and remains stable for a time which is adequate for manipulating it, in aqueous medium, at temperatures of up to 37 to 40° C.

The collagenous material according to the invention can be used for preventing post-operative adhesions.

It can be prepared in a "ready-to-use" form by, for example, cutting a film such as described above to the dimensions which are appropriate for the envisaged application and packing it under sterile conditions.

When the material is prepared in the form of a film, it is particularly suitable for this application, in particular for simplifying and speeding up the surgical procedure.

This is because the collagenous film which is obtained can be manipulated with ease because it is not sticky to the touch in the dry state and it does not stick to instruments.

Furthermore, it has an increased density and mechanical resistance while at the same time being relatively pliable, as is required.

The glycerol improves the pliability of the final material obtained and can thus facilitate its use.

The collagenous material according to the invention is able to develop adhesive properties in aqueous medium.

After having been implanted in a patient, it can adhere adequately to the organ to be protected, thereby enabling it to remain in place, and is for this reason suitable for being used as a post-operative anti-adhesion barrier. Thus, on contact with the tissues, an inflow of tissue water results in immediate adherence of the collagenous film. The inflow of water progressively swells the film of collagen, whose crosslinking is of sufficiently low density to permit a certain degree of mobility and flexibility of the chains which make up the film.

A gel of collagen, which is oxidized, crosslinked and very hydrated due to the hydrophilic additive which is trapped in the meshes of the gel, is thus formed within a few minutes to a few hours.

This gel acquires adhesive properties which are adequate for establishing satisfactory adherence of the biomaterial to the wound to be protected.

Furthermore, the hydrophilic macromolecular additive disappears, by diffusion through the oxidized and crosslinked collagenous material, in a few days, with the swelling of this material favouring its degradation within less than a month, if not to say less than 7 days, in particular in 2 to 3 days.

If the degree of crosslinking of the collagenous material is increased, in particular by means of incubation at 37° C. in a moist environment, before sterilizing by irradiation, it is possible to increase the resorption time to up to 2–4 weeks.

This resorption time of between 1 and 4 weeks is attractive for some applications in which cicatrization of the damaged tissues takes place more slowly.

The invention will be described in more detail with the aid of the examples, which are given below by way of illustration and which are not limiting.

EXAMPLES

Example 1

Preparation of an Acid Precipitate of Collagen which has been Modified by Oxidative Cleavage Using Periodic Acid and which is Not Crosslinked This example is carried out directly on the basis of the previously cited patent of TARDY et al. (1994).

The collagen employed is bovine type I collagen, which is extracted from calf derm by solubilization at acid pH or by digestion with pepsin and purified by salt precipitations using the techniques which have already been described.

The products marketed by COLLAGEN Corp. under the names VITROGEN® or ZYDERM® may be used for this application.

Preference is given to using dry collagen fibres which are obtained by precipitating an acid solution of collagen by means of adding NaCl and then washing and drying the precipitate which is obtained with aqueous solutions of acetone whose concentration increases from 80% to 100%.

Human type I or type III collagens, or a mixture of these collagens in any proportions, can be used in the same way.

A solution of 30 g of collagen/l is prepared by dissolving the collagen in 0.01 N HCl. The volume of the solution is 49 liters. Periodic acid is added to it up to a final concentration of 8 mM, that is 1.83 g/l.

The oxidation is carried out at ambient temperature in the vicinity of 22° C. for 3 hours in the absence of light.

An equal volume of a solution of sodium chloride is then added to the collagen solution in order to obtain a final concentration of 41 g of NaCl/l.

After waiting for 30 minutes, the precipitate is collected by decanting through a wire mesh screen of a porosity of about 100 microns and then washed 4 times with a solution of 41 g of NaCl/l in 0.01 N HCl. 19 kg of acid saline precipitate are obtained. These washes eliminate all traces of periodic acid or iodine-containing derivatives which are formed during the oxidation of the collagen.

Several washes in an 80% aqueous solution of acetone then concentrate the collagen precipitate and remove the salts which are present.

A final wash in 100% acetone results in the preparation of 3.6 kg of a very dense acetone precipitate of acid oxidized collagen which is not crosslinked and which does not contain any other trace of an undesirable chemical product.

Example 2

Preparation of Anti-post-operative Adhesion Collagenous Films According to the Invention The acetone paste prepared as described in Example 1 is taken up in a pyrogenic distilled water at 40° C. in order to obtain a collagen concentration of 3%.

The solution, of 44 liters in volume, is heated at 50° C. for 30 minutes and then filtered under sterile conditions through a membrane having a porosity of 0.45 microns into a tank at 40° C.

A sterile, concentrated solution of PEG 6000 (polyethylene glycol having a molecular weight of 6000 daltons) is added to this solution at 30° C. in order to achieve a PEG concentration of 1%, followed by glycerol in order to achieve a glycerol concentration of 0.6%. The pH of the solution is adjusted to 7.0 by adding concentrated sodium hydroxide solution.

The volume of the solution is then adjusted with sterile water to obtain final concentrations of collagen, PEG and glycerol of 2.7%, 0.9% and 0.54%, respectively, and then distributed in a thin layer, having a density of 0.133 g/cm$^2$, on a flat hydrophobic support of the PVC or polystyrene type. The surfaces are then exposed to a sterile stream of air at ambient temperature, leading to evaporation in approximately 18 hours.

The film which is obtained detaches very readily from the support. It can easily be cut to the dimensions which are required for the experiment.

After that, in order to conform with the pharmaceutical regulations and to improve stability during storage, the film is inserted into a double airtight bag.

The whole is sterilized by beta irradiation and receives a dose which is greater than or equal to 25 kiloGrays.

In general, the dried film still contains residual water up to a concentration which can be as much as 20%.

A typical composition in the example under consideration is 60% by weight of collagen, 20% by weight of PEG, 12% by weight of gylcerol and 8% by weight of water.

The film which is obtained is stable at ambient temperature. It remains stable and easily manipulable after being incubated for 2 hours in water at 37° C.

It is not essential for glycerol to be present in the material; the glycerol improves the flexibility of the film and makes the film easier to use.

This example can be carried out by replacing the PEG 6000 with PEG 3000 or PEG 4000, with soluble starch (OSI France catalogue reference No. A2620) or with DEXTRAN T40 (PHARMACIA Fine Chemicals catalogue, Uppsala, Sweden) or with carboxymethyl cellulose. The concentrations employed, and the mode of operation, are identical.

Study of the Properties of the Collagenous Film According to the Invention in Preventing Post-operative Adhesions.

Toxicology

The collagen/PEG film produced as described in Example 2 (or a ground-up preparation of this film) gives satisfactory results in standardized toxicological tests to which biomaterials for implantation are subjected:

absence of mutagenic character in the AMES test normal, moderate reaction in the delayed hypersensitivity test carried out on guinea-pigs (class III reaction)

absence of systemic toxicity in mice and rats when administered by the intravenous or intraperitoneal route degradation:

in less than 7 days when administered to the rat by the subcutaneous route in 2 to 3 days when administered to the rat by the intraperitoneal route.

Anti-post-operative Adhesion Properties

The anti-post-operative adhesion properties were analysed using the protocol described in the HARRIS et al. (1995) reference.

The protocol described in this publication was carried out on groups of 10 rats.

The tests consist in abrading and dehydrating 2 cm$^2$ areas of the peritoneal wall and caecum which are in contact with each other.

The control group of rats is not given any product for protecting the wounds which have been created in this way. This group is compared with the group of rats which is given a collagen/PEG film as described in Example 2, which film in each case completely covers the wound and extends 5 mm beyond it over the external non-abraded areas.

After a wait of 7 days, in conformity with the published protocol, the results are clear-cut:

no adhesion between the two damaged surfaces is observed in the rat group which is treated with the film of the invention, and the cicatrization of each initial wound is complete no trace of the film is left.

Each of the 10 rats in the control group, which was not treated with the film of the invention, exhibits adhesions, with the characteristics of these adhesions being identical to the results published in the abovementioned HARRIS et al. (1995) document.

When the biodegradable films which were produced as described in Example 2 were tested on other animal models in other operative protocols (WISEMAN 1992 and 1994), they were demonstrated to be effective in preventing adhesions in applications relating to neurosurgery (in particular herniated discs and vertebral laminectomies), to cardiac surgery and to gynaecology, in particular uterine surgery. The invention therefore also relates to using the materials according to the invention in these surgical indications as well as in orthopaedic surgery (in particular in relation to the tendons) and in ophthalmic surgery.

Example 3

Preparation of a Collagenous Film in Accordance with Another Embodiment of the Invention A film is prepared as described in Example 2.

After having been separated from its support and cut, each film is individually packed in a primary bag which is permeable to vapour and then incubated for 12 hours in an incubator which is at 37° C. and whose degree of relative humidity is greater than 80%.

The previous bag is then inserted into a secondary, airtight packaging which is then sterilized as in Example 2.

The material is degraded within 2 to 4 weeks by being implanted subcutaneously or intraperitoneally in rats.

The film according to this example is degraded less rapidly in the organism than is the film of Example 2. It is observed that the film is less adherent to the tissue wound and that it swells less in physiological medium. Because of this, a material of this nature would preferably be indicated in surgical applications where the risk of the material being displaced is low. For other applications, it would be preferable to attach the film using appropriate means (glue, sutures, etc.). Under these conditions, the same antiadhesion properties are observed in vivo.

REFERENCES

1. DI ZEREGA G. S. (1994)—"Contemporary adhesion prevention" *Fertility and Sterility* 61(2), 219–235.
2. HARRIS E. S.—MORGAN R. F.—RODEHEAVER G. T. (1995)—"Analysis of the kinetics of peritoneal adhesion formation in the rat and evaluation of potential antiadhesive agents", *Surgery,* 117(6), 663–669.
3. BECKER J. M.—DAYTON M. T.—FAZIO V. W.—BECK D. E.—STRYKER S. J.—WEXNER S. D.—WOLFF B. G.—ROBERTS P. L.—SMITH L. E.—SWEENEY S. A.—MOORE M. (1996)—"Prevention of postoperative abdominal adhesions by a sodium hyaluronate-based bioresorbable membrane: A prospective, randomized, double-blind multicenter study", *The J. of Amer. College of Surgeons,* 183(4), 297–306.
4. KHOURY W.—ABDUL-MALAK N.—HUC A. (1994)—"Membrane collagénique anti-adhérence post-opératoire (Collagenous anti-post-operative adhesion membrane)", patent application No. 94 06995 of Jun. 8, 1994 in France (published under No. 2 720 945).
5. TAYOT J. L.—MARESCAUX J.—DUMAS H.—TARDY M. (1988)—"Visceral surgery patch", U.S. Pat. No. 5,201,745, issued on Apr. 13, 1993 (under the priority of French patent application No. 88 03321 of Mar. 15, 1988, issued on Jul. 13, 1990 under No. 2 628 634).
6. ORLY I. (1994)—"Use of collagen membranes as peritoneal renewing prostheses", international patent application WO 96/08277 (under the priority of French patent application No. 94 11 015 of Sep. 9, 1994).
7. YEUNG J. E.—CHU G. H.—DE LUSTRO F. A.—RHEE W. M. (1995)—"Anti adhesion films and compositions for medical use", European patent application No. 96 102 339.7 (published under No. 0 732 110) (under the priority of American patent application serial No. 403 360 of Mar. 14, 1995).
8. TARDY M.—TIOLLIER J.—TAYOT J. L. (1994)—"Composition adhésive, á usage chirurgical, á base de collagéne modifié par coupure oxydative et non réticulé (Adhesive composition for surgical use, based on collagen which is modified by oxidative cleavage and which is not crosslinked)" —French patent application No. 94 00715 of Jan. 24, 1994, issued on Aug. 2, 1996 under No. 2 715 309.
9. TARDY M.—TAYOT J. L. (1986)—"Process for the treatment of collagen, notably for facilitating its cross-linking, and the collagen obtained by the application of the said process", patent U.S. Pat. No. 4,931,546 issued on May 6, 1990 (under the priority of French patent application No. 86 10 160 of Jul. 11, 1986, issued on May 12, 1989 under No. 2 601 371).
10. WISEMAN D. "Polymers for the prevention of surgical adhesions" in Polymeric Site-specific pharmaco-therapy, Ed. A. J. DOMB, John Wiley & Sons Ltd, 1994.

11. WISEMAN D. et al., "Fibrinolytic drugs prevent pericardial adhesions in the rabbit" J. of Surgical Research 53, 362–368, 1992.

What is claimed is:

1. Non-toxic biocompatible collagenous material, comprising collagen having at least partially lost its helical structure and having been crosslinked in the presence of an, and one hydrophilic macromolecular additive comprising a polyethylene glycol which is chemically non-reactive towards the collagen, whereby said material is not sticky in the dry state, is adhesive to body tissues in presence of aqueous medium, and is biodegradable in less than one month.

2. Collagenous material according to claim 1, characterized in that it is boidegradable within less than one week.

3. Collagenous material according to claim 1, characterized in that the collagen at least partially lost its helical structure by being submitted to moderate heating above 37° C.

4. Collagenous material according to claim 1, characterized in that the hydrophilic macromolecular additive has a molecular weight greater than 3000 daltons.

5. Collagenous material according to claim 4, characterized in that it is cross-linked by beta irradiation or gamma irradiation in the presence of said hydrophilic macromolecular additive which is chemically non-reactive towards the collagen.

6. Collagenous material according to claim 1, wherein the hydrophilic additive, further comprises a hydrophilic polymer having a molecular weight of between 3000 and 20,000 daltons.

7. Collagenous material according to claim 1, wherein the hydrophilic additive consists substantially of polyethylene glycol.

8. Collagenous material according to claim 1, wherein the hydrophilic additive further comprises a polysaccharide which is selected from the consisting of starch, dextran and cellulose.

9. Collagenous material according to claim 1, characterized in that it comprises collagen and at least one hydrophilic macromolecular additive in accordance with a collagen/hydrophilic additive(s) ratio of from 1/1 to 9/1.

10. Collagenous material according to claim 1, characterized in that it additionally contains glycerol.

11. Collagenous material according to claim 1, characterized in that it is present in the form of a film.

12. Collagenous material according to claim 1, characterized in that the material is subjected to irradiation with beta radiation.

13. Collagenous material according to claim 12, characterized in that the material is subjected to beta irradiation at a dose which is greater than or equal to 25 kilogreys.

14. Collagenous material according to claim 1 wherein the collagen was submitted to a digestion with pepsin.

15. Collagenous material according to claim 1 wherein the collagen at least partially lost its helical structure by subjecting the collagen to heating at a temperature not higher than 50° C.

16. Collagenous material according to claim 15 wherein the collagen at least partially lost its helical structure by subjecting the collagen to heating at a temperature between 40 and 50° C.

17. Collagenous material according to claim 1, wherein the collagenous material comprises collagen and at least one hydrophilic macromolecular additive comprising polyethylene glycol in accordance with a collagen/hydrophilic additive(s) ratio of from 2/1 to 4/1.

18. Collagenous material according to claim 1, wherein the collagenous material comprises collagen and at least one hydrophilic macromolecular additive comprising polyethylene glycol in accordance with a collagen/hydrophilic additive(s) ratio of 3/1.

19. Process for obtaining a biocompatible collagenous material which is non-toxic, non-sticky in the dry state and adhesive to body tissues in the presence of an aqueous medium and biodegradable in less than one month, characterized in that it comprises:
   a) preparing a collagen solution;
   b) treating the said solution in order to cause the collagen at least partially to lose its helical structure;
   c) mixing the resulting collagenous solution with a solution containing at least one hydrophilic macromolecular additive comprising a polyethylene glycol which is chemically non-reactive towards the collagen which is present;
   d) cross-linking the said mixture in order to obtain the desired collagenous material.

20. Process according to claim 19, wherein step a) comprises modifying the solution of collagen by oxidative cleavage.

21. Process according to claim 20, characterized in that, in step a), an acid solution of collagen having a concentration of between 5 and 50 g/l is prepared and then mixed, at ambient temperature, with a solution of periodic acid or one of its salts at a concentration of between 1 and $10^{-5}$ M.

22. Process according to claim 20, characterized in that, in step d), the mixture is neutralized to neutral pH.

23. Process according to any one of claim 19, characterized in that, in step b), the solution of collagen is treated by being heated at a temperature greater than 37° C.

24. Process according to claim 23, characterized in that, in step b), the solution of collagen is heated at a temperature of between 40 and 50° C.

25. Process according to claim 19, characterized in that, in step c), the hydrophilic additive has a molecular weight which is greater than 3000 daltons.

26. Process according to claim 19, wherein, in step c), the hydrophilic additive further comprises a hydrophilic polymer having a molecular weight of between 3000 and 20,000 daltons.

27. Process according to claim 19, wherein, in step c), the hydrophilic additive consists substantially of polyethylene glycol.

28. Process according to claim 19, wherein in step c), the at least one hydrophilic additive further comprises a polysaccharide which is selected from the group consisting of starch, dextran and cellulose.

29. Process according to claim 19, characterized in that, in step c), the concentration of hydrophilic additive is from 2 to 10 times lower than that of the collagen.

30. Process according to claim 19, characterized in that, in step c), glycerol is additionally added.

31. Process according to claim 30, characterized in that the concentration of glycerol is between 3 and 8 g/l.

32. Process according to claim 19, characterized in that, in step d), the mixture is cross-linked by beta or gamma radiation.

33. Process according to claim 19, characterized in that the collagenous material derived from step d) is subjected to irradiation with beta radiation.

34. Process according to claim 33, characterized in that the collagenous material is subjected to beta irradiation at a dose which is greater than or equal to 25 kilogreys.

35. Process according to claim 19, characterized in that a film is formed from the solution containing collagen, which has at least partially lost its helical structure and which may have been modified by oxidative cleavage, at least one hydrophilic additive comprising polyethylene glycol and, where appropriate, glycerol.

36. Process according to claim 35, characterized in that a thin layer of the solution is substantially uniformly applied to an inert support which is substantially flat, the collagen is allowed to cross-link and the film which has formed is then separated from the support.

37. Process according to claim 35, characterized in that the solution contains from 2 to 6% collagen, from 0.6 to 2% hydrophilic additive and from 0.3 to 0.8% glycerol, and the thin layer which is applied to the said inert support has a density of between 0.05 and 0.3 g/cm$^2$.

38. Process according to claim 19, characterized in that the cross-linked collagen is subjected to an incubation at 37° C. in a moist environment before the step of being sterilized by irradiation, with the material obtained being biodegradable within 2 to 4 weeks.

39. Process according to claim 19 characterized in that the collagen solution of step a) is a solution of collagen which was submitted to a digestion with pepsin.

40. A method for preventing post-operative adhesions, which comprises:
  applying to tissues to be protected, a non-toxic biocompatible collagenous material which is biodegradable in less than one month, comprising collagen having at least partially lost its helical structure and being crosslinked in the presence of at least one hydrophilic macromolecular additive comprising a polyethylene glycol which is chemically non-reactive towards the collagen; and
  allowing said collagenous material to swell on contact with the tissues, the gel of oxidized, cross-linked and very hydrated collagen thus obtained developing adhesive properties adequate for establishing satisfactory adherence of the collagenous material to the tissues to be protected.

41. The method according to claim 40, characterized in that collagenous material is biodegradable within less than one week.

42. The method according to claim 40, wherein the collagen at least partially lost its helical structure by being heated above 37° C.

43. The method according to claim 40, wherein the collagenous material comprises collagen subjected to oxidative cleavage and cross-linked in the presence of at least one hydrophilic macromolecular additive comprising a polyethylene glycol which is chemically non-reactive towards the collagen.

44. The method according to claim 43, wherein the collagen is subjected to oxidative cleavage using periodic acid or one of its salts.

45. The method according to claim 40, characterized in that the collagenous material is cross-linked by beta irradiation or gamma irradiation in the presence of a hydrophilic macromolecular additive comprising a polyethylene glycol which is chemically non-reactive towards the collagen.

46. The method according to claim 40, wherein the hydrophilic macromolecular additive further comprises a molecule having a molecular weight greater than 3000 daltons.

47. The method according to claim 40, wherein the hydrophilic macromolecule additive further comprises a hydrophilic polymer having a molecular weight of between 3000 and 20,000 daltons.

48. The method according to claim 40, characterized in that the hydrophilic additive consists substantially of polyethylene glycol.

49. The method according to claim 40, wherein the hydrophilic additive further comprises a polysaccharide which is preferably selected from starch, dextran and cellulose.

50. The method according to claim 40, wherein the collagenous material comprises collagen and at least one hydrophilic macromolecular additive comprising a polyethylene glycol in accordance with a collagen/hydrophilic additive(s) ratio of from 1/1 to 9/1.

51. The method according to claim 40, characterized in that the collagenous material additionally contains glycerol.

52. The method according to claim 40, characterized in that the collagenous material is present in the form of a film.

53. The method according to claim 40, characterized in that the collagen was submitted to a digestion with pepsin.

54. The method according to claim 40, characterized in that the collagenous material is subjected to irradiation with beta radiation.

55. The method according to claim 54, characterized in that the collagenous material is subjected to beta irradiation at a dose which is greater than or equal to 25 kilograys.

56. The method according to claim 40, wherein the collagenous material comprises collagen and at least one hydrophilic macromolecular additive comprising polyethylene glycol in accordance with a collagen/hydrophilic additive(s) ratio of from 2/1 to 4/1.

57. The method according to claim 40, wherein the collagenous material comprises collagen and at least one hydrophilic macromolecular additive comprising polyethylene glycol in accordance with a collagen/hydrophilic additive(s) ratio of 3/1.

58. Non-toxic biocompatible collagenous material, comprising:
  collagen having at least partially lost its helical structure and being cross-linked after oxidative cleavage and
  one hydrophilic macromolecular additive comprising a polyethylene glycol which is chemically non-reactive towards the collagen, said collagen having been crosslinked in the presence of said hydrophilic macromolecular additive,
  whereby said material is not sticky in the dry state, is adhesive to body tissues in presence of aqueous medium, and is biodegradable in less than one month.

59. Collagenous material according to claim 58 wherein the collagen was submitted to a digestion with pepsin.

60. Collagenous material according to claim 58, wherein the collagen at least partially lost its helical structure by being submitted to moderate heating above 37° C.

61. Collagenous material according to claim 60 wherein the collagen is heated at a temperature not higher than 50° C.

62. Collagenous material according to claim 61, wherein the collagen is heated at a temperature between 40 and 50° C.

63. Collagenous material according to claim 58, characterized in that it is biodegradable within less than one week.

64. Collagenous material according to claim 58, wherein the collagen at least partially lost its helical structure by being heated by moderate heating above 37° C.

65. Collagenous material according to claim 58, wherein the collagen is was subjected to oxidative cleavage using periodic acid or one of its salts.

66. Collagenous material according to claim 58 characterized in that it is sterilized by beta irradiation or gamma irradiation in the presence of said hydrophilic macromolecular additive which is chemically non-reactive towards the collagen.

67. Collagenous material according to claim 58, wherein the hydrophilic macromolecular additive further comprises a molecule having a molecular weight greater than 3000 daltons.

68. Collagenous material according to claim 67, characterized in that the material is subjected to beta irradiation at a dose which is greater than or equal to 25 kilograys.

69. Collagenous material according to claim 58, wherein the hydrophilic additive further comprises a hydrophilic polymer having a molecular weight of between 3000 and 20,000 daltons.

70. Collagenous material according to claim 58, wherein the hydrophilic additive consists substantially of polyethylene glycol.

71. Collagenous material according to claim 58, wherein the hydrophilic additive further comprises a polysaccharide which is selected from starch, dextran and cellulose.

72. Collagenous material according to claim 58, wherein said collagenous material comprises collagen and at least one hydrophilic macromolecular additive comprising polyethylene glycol in accordance with a collagen/hydrophilic additive(s) ratio of from 1/1 to 9/1.

73. Collagenous material according to claim 58, characterized in that it additionally contains glycerol.

74. Collagenous material according to claim 58, characterized in that it is present in the form of a film.

75. Collagenous material according to claim 58 characterized in that the material is subjected to irradiation with beta radiation.

76. Collagenous material according to claim 58, wherein the collagenous material comprises collagen and at least one hydrophilic macromolecular additive comprising polyethylene glycol in accordance with a collagen/hydrophilic additive(s) ratio of from 2/1 to 4/1.

77. Collagenous material according to claim 58, wherein the collagenous material comprises collagen and at least one hydrophilic macromolecular additive comprising polyethylene glycol in accordance with a collagen/hydrophilic additive(s) ratio of 3/1.

78. Non-toxic biocompatible collagenous material, comprising:
collagen having at least partially lost its helical structure, which was submitted to a digestion with pepsin, to a moderate heating above 37° C. and to a cross-linking treatment after oxidative cleavage of the collagen, in the presence of at lease one hydrophilic macromolecular additive comprising a polyethylene glycol which is chemically non-reactive towards the collagen, whereby said material is not sticky in the dry state, is adhesive to body tissues in presence of aqueous medium and is biodegradable in less than one month.

79. Collagenous material according to claim 78 wherein the collagen is heated at a temperature not higher than 50° C.

80. Collagenous material according to claim 78, wherein the collagen is heated at a temperature between 40 and 50° C.

81. Collagenous material according to claim 78, characterized in that it is biodegradable within less than one week.

82. Collagenous material according to claim 78, wherein the collagen is was subjected to oxidative cleavage using periodic acid or one of its salts.

83. Collagenous material according to claim 78 characterized in that it is cross-linked in the presence of said hydrophilic macromolecular additive which is chemically non-reactive towards the collagen.

84. Collagenous material according to claim 78, wherein the hydrophilic macromolecular additive further comprises a macromolecule having a molecular weight greater than 3000 daltons.

85. Collagenous material according to claim 78, wherein the hydrophilic additive further comprises a hydrophilic polymer having a molecular weight of between 3000 and 20,000 daltons.

86. Collagenous material according to claim 78, wherein the hydrophilic additive consists substantially of polyethylene glycol.

87. Collagenous material according to claim 78, wherein the hydrophilic additive further comprises a polysaccharide which is selected from starch, dextran and cellulose.

88. Collagenous material according to claim 78, wherein said collagenous material comprises collagen and at least one hydrophilic macromolecular additive comprising polyethylene glycol in accordance with a collagen/hydrophilic additive(s) ratio of from 1/1 to 9/1.

89. Collagenous material according to claim 78 characterized in that it additionally contains glycerol.

90. Collagenous material according to claim 78 characterized in that it is present in the form of a film.

91. Collagenous material according to claim 78 characterized in that the material is subjected to irradiation with beta radiation.

92. Collagenous material according to claim 78, characterized in that the material is subjected to beta irradiation at a dose which is greater than or equal to 25 kilogreys.

93. Collagenous material according to claim 78, wherein the collagenous material comprises collagen and at least one hydrophilic macromolecular additive comprising polyethylene glycol in accordance with a collagen/hydrophilic additive(s) ratio of from 2/1 to 4/1.

94. Collagenous material according to claim 78, wherein the collagenous material comprises collagen and at least one hydrophilic macromolecular additive comprising polyethylene glycol in accordance with a collagen/hydrophilic additive(s) ratio of 3/1.

95. Non-toxic biocompatible collagenous material, comprising collagen having at least partially lost its helical structure, which was submitted to a moderate heating above 37° C., and cross-linked after oxidative cleavage in the presence of at least one hydrophilic macromolecular additive comprising a polyethylene glycol which is chemically non-reactive towards the collagen and has a molecular weight of at least 3000 daltons, whereby said material is not sticky in the dry state, is adhesive to body tissues in presence of aqueous medium, and is biodegradable in less than one month.

96. Collagenous material according to claim 95, wherein the collagen is heated at a temperature not higher than 50° C.

97. Collagenous material according to claim 95, wherein the collagen is heated at a temperature between 40 and 50° C.

98. Collagenous material according to claim 95, wherein the collagen was subjected to oxidative cleavage using periodic acid or one of its salts.

99. Collagenous material according to claim 95, wherein the hydrophilic additive consists substantially of polyethylene glycol.

100. Collagenous material according to claim 95, wherein the hydrophilic additive further comprises a polysaccharide which is selected from starch, dextran and cellulose.

101. Collagenous material according to claim 95, wherein the collagenous material comprises collagen and at least one hydrophilic macromolecular additive comprising polyethylene glycol in accordance with a collagen-hydrophilic additive(s) ratio of from 1/1 to 9/1.

102. Collagenous material according to claim 95, characterized in that it additionally contains glycerol.

103. Collagenous material according to claim 95, characterized in that it is present in the form of a film.

104. Collagenous material according to claim 95, characterized in that the material is subjected to irradiation with beta radiation.

105. Collagenous material according to claim 95, characterized in that the material is subjected to beta irradiation at a dose which is greater than or equal to 25 kilogreys.

106. Collagenous material according to claim 85, wherein the collagenous material comprises collagen and at least one hydrophilic macromolecular additive comprising polyethylene glycol in accordance with a collagen-hydrophilic additive(s) ratio of from 2/1 to 4/1.

107. Collagenous material according to claim 95, wherein the collagenous material comprises collagen and at least one hydrophilic macromolecular additive comprising polyethylene glycol in accordance with a collagen-hydrophilic additive(s) ratio of 3/1.

* * * * *